(12) United States Patent
Amanullah (10) Patent No.: US 10,781,354 B2
(45) Date of Patent: *Sep. 22, 2020

(54) DATE TREE WASTE-BASED COMPOUND FIBROUS LCMS

(71) Applicant: Saudi Arabian Oil Company, Dhahran (SA)

(72) Inventor: Md Amanullah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,738

(22) Filed: Mar. 13, 2018

(65) Prior Publication Data
US 2018/0201819 A1  Jul. 19, 2018

Related U.S. Application Data

(62) Division of application No. 15/436,129, filed on Feb. 17, 2017.

(60) Provisional application No. 62/356,862, filed on Jun. 30, 2016.

(51) Int. Cl.
*C09K 8/035* (2006.01)
*C09K 8/514* (2006.01)

(52) U.S. Cl.
CPC ............ *C09K 8/035* (2013.01); *C09K 8/514* (2013.01); *C09K 2208/04* (2013.01); *C09K 2208/08* (2013.01)

(58) Field of Classification Search
CPC .... C09K 8/035; C09K 8/514; C09K 2208/04; C09K 2208/08
See application file for complete search history.

(56) References Cited

U.S. PATENT DOCUMENTS

| 2,483,936 | A | 10/1949 | Roberts |
| 2,600,404 | A | 6/1952 | Hoeppel |
| 2,749,308 | A | 6/1956 | Beckum et al. |
| 2,779,417 | A | 1/1957 | Clark, Jr. et al. |
| 2,789,948 | A | 4/1957 | Tronolone |
| 2,811,488 | A | 10/1957 | Nestle et al. |
| 2,912,380 | A | 11/1959 | Groves |
| 2,943,679 | A | 7/1960 | Scott, Jr. |
| 2,943,680 | A | 7/1960 | Scott et al. |
| 3,147,127 | A | 9/1964 | Shannon |
| 4,086,098 | A | 4/1978 | Le Ruyet et al. |
| 4,110,225 | A | 8/1978 | Cagle |
| 4,127,548 | A | 11/1978 | Alexander |
| 4,275,788 | A | 6/1981 | Sweatman |
| 4,619,772 | A | 10/1986 | Black et al. |
| 5,004,553 | A | 4/1991 | House et al. |
| 5,118,664 | A | 6/1992 | Burts, Jr. |
| 5,197,324 | A | 3/1993 | Keys |
| 5,332,724 | A | 7/1994 | Burts, Jr. |
| 5,484,028 | A | 1/1996 | Rose |
| 5,501,275 | A | 3/1996 | Card et al. |
| 5,801,127 | A | 9/1998 | Duhon, Sr. |
| 6,016,879 | A | 1/2000 | Burts, Jr. |
| 6,098,712 | A | 8/2000 | Burts, Jr. |
| 6,102,121 | A | 8/2000 | Burts, Jr. |
| 6,271,001 | B1 | 8/2001 | Clarke et al. |
| 6,350,594 | B1 | 2/2002 | Clarke et al. |
| 6,518,224 | B2 | 2/2003 | Wood |
| 6,716,798 | B1 | 4/2004 | Burts, Jr. |
| 6,750,179 | B1 | 6/2004 | Burts, Jr. |
| 6,790,812 | B2 | 9/2004 | Halliday |
| 6,806,232 | B1 | 10/2004 | Cart |
| 6,814,798 | B2 | 11/2004 | Vijn et al. |
| 6,861,392 | B2 | 3/2005 | Shaarpour |
| 6,932,158 | B2 | 8/2005 | Burts |
| 7,226,895 | B2 | 6/2007 | Xiang |
| 7,271,131 | B2 | 9/2007 | Halliday et al. |
| 7,284,611 | B2 | 10/2007 | Reddy et al. |
| 7,297,662 | B2 | 11/2007 | Verret |
| 7,297,663 | B1 | 11/2007 | Kilchrist et al. |

(Continued)

FOREIGN PATENT DOCUMENTS

| CN | 101311243 A | 11/2008 |
| CN | 101560084 A | 10/2009 |

(Continued)

OTHER PUBLICATIONS

Alawad, Musaed N.J., et al.; "Superior fracture-seal material using crushed date palm seeds for oil and gas well drilling operations" Journal of King Saud University—Engineering Sciences (2017); pp. 1-7.

Al-Awad, Musaed NJ et al.; "Utilization of Shredded Waste Car Tyres as a Fracture Seal Material (FSM) in Oil and Gas Drilling Operations" Journal of Petroleum & Environmental Biotechnology, (2017) vol. 8, Issue 2; pp. 1-4.

International Search Report and Written Opinion for International Application No. PCT/US2018/034291 (SA5652/PCT); International Filing Date May 24, 2018; Report dated Jul. 31, 2018 (pp. 1-11).

(Continued)

*Primary Examiner* — Frances Tischler
(74) *Attorney, Agent, or Firm* — Bracewell LLP; Constance G. Rhebergen; Brian H. Tompkins (57) ABSTRACT

A date tree waste-based lost circulation material (LCM) is provided. The date tree waste LCM may include includes fibers from the date tree waste produced from processing date trees in the production of date fruits. The date tree waste may include fibers from one or more of the following: date tree trunks, date tree rachis, date tree leaflets, date tree panicles, and date tree roots. The date tree waste LCM may include fibers having lengths in the range of 5 millimeters (5 mm) to 15 mm, diameters in the range of 0.5 mm to 0.8 mm, and having an aspect ratio range of 6 to 30. Methods of lost circulation control using and manufacture of a date tree waste LCM are also provided.

2 Claims, 7 Drawing Sheets

(56) References Cited

U.S. PATENT DOCUMENTS

| | | |
|---|---|---|
| 7,332,026 B2 | 2/2008 | Fyten et al. |
| 7,488,705 B2 | 2/2009 | Reddy et al. |
| 7,507,692 B2 | 3/2009 | Kiang |
| 7,537,054 B2 | 5/2009 | Reddy et al. |
| 7,629,297 B2 | 12/2009 | Shaarpour |
| 7,744,689 B2 | 6/2010 | Hojaji et al. |
| 7,902,126 B1 | 3/2011 | Burts, Jr. |
| 7,923,413 B2 | 4/2011 | Ghassemzadeh |
| 7,964,537 B2 | 6/2011 | Rayborn, Sr. et al. |
| 8,371,381 B2 | 2/2013 | Shindgikar et al. |
| 8,383,558 B2 | 2/2013 | Reddy et al. |
| 8,404,622 B2 | 3/2013 | Ghassemzadeh |
| 8,673,825 B2 | 3/2014 | Rayborn, Sr. et al. |
| 8,739,872 B1 | 6/2014 | Miller et al. |
| 8,776,882 B2 | 7/2014 | Shindgikar et al. |
| 8,887,808 B2 | 11/2014 | Kumar et al. |
| 8,935,957 B2 | 1/2015 | Kulkarni et al. |
| 8,992,670 B1 | 3/2015 | Vohra |
| 9,140,118 B2 | 9/2015 | Kulkarni et al. |
| 9,175,529 B2 | 11/2015 | Jamison et al. |
| 9,376,607 B2 | 6/2016 | James |
| 9,410,066 B2 | 8/2016 | Ghassemzadeh |
| 9,416,306 B2 | 8/2016 | Savari et al. |
| 9,453,156 B2 | 9/2016 | Wu |
| 9,505,659 B2 | 11/2016 | Bickbau |
| 9,592,488 B2 | 3/2017 | Yusuf et al. |
| 9,623,067 B1 | 4/2017 | Awad et al. |
| 9,688,901 B2 | 6/2017 | Fontenot |
| 9,783,727 B2 | 10/2017 | Lahman et al. |
| 10,087,353 B2 | 10/2018 | Amanullah |
| 10,352,116 B2 | 7/2019 | Amanullah |
| 10,597,575 B2 | 3/2020 | Amanullah et al. |
| 10,611,944 B2 | 4/2020 | Amanullah |
| 10,611,945 B2 | 4/2020 | Amanullah |
| 10,611,946 B2 | 4/2020 | Amanullah |
| 10,619,433 B2 | 4/2020 | Amanullah |
| 2002/0010100 A1 | 1/2002 | Wood |
| 2004/0023813 A1 | 2/2004 | Burts, III |
| 2004/0129460 A1 | 7/2004 | MacQuoid et al. |
| 2004/0244978 A1 | 12/2004 | Shaarpour |
| 2005/0113260 A1 | 5/2005 | Wood |
| 2005/0124502 A1 | 6/2005 | Shaarpour |
| 2005/0217852 A1 | 10/2005 | Bennett et al. |
| 2006/0106136 A1 | 5/2006 | Abu-Sharkh |
| 2006/0122069 A1 | 6/2006 | Burts, III |
| 2006/0157247 A1 | 7/2006 | Burts, III |
| 2006/0160907 A1 | 7/2006 | Stamp |
| 2009/0054269 A1 | 2/2009 | Chatterji et al. |
| 2009/0286697 A1 | 11/2009 | Shaarpour |
| 2009/0305038 A1 | 12/2009 | Duran et al. |
| 2009/0305911 A1 | 12/2009 | Pomerleau |
| 2010/0152070 A1 | 6/2010 | Ghassemzadeh |
| 2010/0181110 A1 | 7/2010 | Harr |
| 2010/0193244 A1 | 8/2010 | Hoskins |
| 2010/0230164 A1 | 9/2010 | Pomerleau |
| 2010/0230169 A1 | 9/2010 | Pomerleau |
| 2011/0214870 A1 | 9/2011 | Shaarpour |
| 2011/0278006 A1 | 11/2011 | Sanders |
| 2012/0157354 A1 | 6/2012 | Li et al. |
| 2012/0247763 A1 | 10/2012 | Rakitsky et al. |
| 2013/0025863 A1 | 1/2013 | Lin et al. |
| 2014/0038857 A1* | 2/2014 | Miller .................... C09K 8/035 507/104 |
| 2014/0102987 A1 | 4/2014 | Yusuf et al. |
| 2014/0110177 A1 | 4/2014 | Harr |
| 2014/0135237 A1 | 5/2014 | Villarreal, Jr. et al. |
| 2014/0209290 A1 | 7/2014 | Jamison et al. |
| 2014/0231082 A1 | 8/2014 | Jamison et al. |
| 2014/0262281 A1 | 9/2014 | Kulkarni et al. |
| 2014/0318793 A1 | 10/2014 | Van Petergem et al. |
| 2014/0353043 A1 | 12/2014 | Amanullah et al. |
| 2015/0008044 A1 | 1/2015 | Fontenot |
| 2015/0051120 A1 | 2/2015 | Hurd et al. |
| 2015/0072901 A1 | 3/2015 | Samuel et al. |
| 2015/0166875 A1 | 6/2015 | Bird et al. |
| 2015/0247081 A1 | 9/2015 | Dillon et al. |
| 2015/0251156 A1 | 9/2015 | Yusuf et al. |
| 2016/0060985 A1 | 3/2016 | Lin et al. |
| 2016/0096988 A1 | 4/2016 | Lin et al. |
| 2016/0177164 A1 | 6/2016 | Dillon et al. |
| 2016/0222274 A1 | 8/2016 | Hoskins |
| 2016/0222275 A1 | 8/2016 | Galindo et al. |
| 2016/0257869 A1 | 9/2016 | Kulkarni et al. |
| 2016/0264839 A1 | 9/2016 | Mata et al. |
| 2016/0289528 A1 | 10/2016 | Wagle et al. |
| 2016/0312100 A1 | 10/2016 | Amanullah et al. |
| 2017/0058180 A1 | 3/2017 | Hossain et al. |
| 2017/0137688 A1 | 5/2017 | Amanullah |
| 2017/0166795 A1 | 6/2017 | Walker et al. |
| 2017/0240791 A1* | 8/2017 | Padua Oliveira ........ C09K 8/03 |
| 2017/0298263 A1 | 10/2017 | Amanullah |
| 2018/0002588 A1 | 1/2018 | Amanullah |
| 2018/0002589 A1 | 1/2018 | Amanullah |
| 2018/0016483 A1 | 1/2018 | Amanullah |
| 2018/0057729 A1 | 3/2018 | Amanullah |
| 2018/0340109 A1 | 11/2018 | Amanullah |
| 2019/0177593 A1 | 6/2019 | Amanullah |
| 2019/0177594 A1 | 6/2019 | Amanullah |
| 2019/0177595 A1 | 6/2019 | Amanullah |
| 2019/0185731 A1 | 6/2019 | Amanullah |
| 2019/0185732 A1 | 6/2019 | Amanullah |
| 2019/0194519 A1 | 6/2019 | Amanullah |
| 2019/0218869 A1 | 7/2019 | Amanullah |
| 2019/0218870 A1 | 7/2019 | Amanullah |
| 2019/0233705 A1 | 8/2019 | Amanullah et al. |
| 2019/0270924 A1 | 9/2019 | Amanullah |
| 2019/0375973 A1 | 12/2019 | Amanullah |
| 2020/0002592 A1 | 1/2020 | Amanullah |
| 2020/0079987 A1 | 3/2020 | Amanullah |
| 2020/0079988 A1 | 3/2020 | Amanullah |

FOREIGN PATENT DOCUMENTS

| | | | |
|---|---|---|---|
| CN | 101724383 A | 6/2010 | |
| CN | 102127403 A | 7/2011 | |
| CN | 203035080 U | 7/2013 | |
| CN | 103570298 A | 2/2014 | |
| CN | 103740346 A | 4/2014 | |
| CN | 104087274 A | 10/2014 | |
| CN | 104419392 A | 3/2015 | |
| CN | 105541159 A | 5/2016 | |
| GB | 2506603 A | 4/2014 | |
| JP | 0671171 A | 3/1994 | |
| WO | 200153429 A1 | 7/2001 | |
| WO | 2004013448 A2 | 2/2004 | |
| WO | 2010019535 A2 | 2/2010 | |
| WO | 2010088484 A2 | 8/2010 | |
| WO | 2010142370 A1 | 12/2010 | |
| WO | 2012037600 A1 | 3/2012 | |
| WO | 2012061187 A2 | 5/2012 | |
| WO | 2013039938 A1 | 3/2013 | |
| WO | 2014008598 A1 | 1/2014 | |
| WO | 2014197417 A1 | 12/2014 | |
| WO | 2015142156 A1 | 9/2015 | |
| WO | 2015199652 A1 | 12/2015 | |
| WO | 2016019416 A1 | 2/2016 | |
| WO | 2016028470 A1 | 2/2016 | |
| WO | WO-2016028470 A1 * | 2/2016 | ............... C09K 8/03 |
| WO | 2016172287 A1 | 10/2016 | |
| WO | 2017087434 A1 | 5/2017 | |
| WO | 2018005575 A1 | 1/2018 | |
| WO | 2018013619 A1 | 1/2018 | |

OTHER PUBLICATIONS

Saudi Aramco "Local pal trees support technical solutions" Dhahran, Aug. 4, 2015; available as of Sep. 19, 2018 at the website: www.saudiaramco.com/en/home/news-media/news/local-palm-trees-support.html.

International Search Report and Written Opinion for International Application No. PCT/US2017/027287 (SA5508/PCT); report dated Sep. 13, 2017; 11 pages.

(56) References Cited

OTHER PUBLICATIONS

International Search Report and Written Opinion for International Application No. PCT/US2017/041611 (SA5534); International Filing Date Jul. 12, 2017; Report dated Oct. 27, 2017 (pp. 1-15).

International Search Report and Written Opinion for International Application No. PCT/US2018/048423 (SA5757); International Filing Date Aug. 29, 2018; Report dated Nov. 29, 2018 (pp. 1-12).

Alsaba, M. et al. "Review of lost circulation materials and treatments with an updated classification." AADE National Technical Conference and Exhibition, Houston, TX, Apr. 2014; pp. 1-9.

Amanullah "Characteristics, behavior and performance of ARC Plug-A date seed-based sized particulate LCM." SPE Kingdom of Saudi Arabia Annual Technical Symposium and Exhibition. Society of Petroleum Engineers, 2016; pp. 1-9.

Amanullah, et al.: "Application of an indigenous eco-friendly raw material as fluid loss additive", Journal of Petroleum Science and Engineering, vol. 139, (2016); pp. 191-197.

BakerHughes.com "SOLUFLAKE Flaked Calcium Carbonate" (XP055401101) Jan. 8, 2016; p. 1.

International Search Report and Written Opinion for International Application No. PCT/US2016/062130 (SA5410/PCT); Report dated Jan. 27, 2017; pp. 1-12.

International Search Report and Written Opinion for International Application No. PCT/US2017/039614 (SA5532/PCT); Report dated Sep. 11, 2017; pp. 1-12.

International Search Report and Written Opinion for International Application No. PCT/US2017/039616 (SA5533/PCT); Report dated Sep. 11, 2017; pp. 1-11.

International Search Report and Written Opinion for International Application No. PCT/US2017/053355 (SA5580/PCT); International filing date Sep. 26, 2017; Report dated Jan. 17, 2018; pp. 1-14.

International Search Report and Written Opinion for International Application No. PCT/US2017/060079 (SA5577/PCT); International Filing Date Nov. 6, 2017; Report dated Dec. 18, 2017; pp. 1-14.

International Search Report and Written Opinion for International Application No. PCT/US2017/067179 (SA5600/PCT) International Filing Date Dec. 19, 2017; Report dated Feb. 21, 2018; pp. 1-14.

International Search Report and Written Opinion for International Application No. PCT/US2017/047877 (SA5599/PCT); Report dated Oct. 27, 2017; pp. 1-15.

Wajheeuddin, et al. "An experimental study on particle sizing of natural substitutes for drilling fluid applications." Journal of Nature Science and Sustainable Technology 8.2 (2014): pp. 1-14.

International Search Report and Written Opinion for International Application No. PCT/US2019/016614 (SA5796) report dated Jun. 3, 2019; pp. 1-12.

International Search Report and Written Opinion for International Application No. PCT/US2019/022843 (SA5854) report dated Jun. 3, 2019; pp. 1-13.

Wajheeuddin, Mohammed; "Development of an Environmentally-Friendly Drilling Fluid Using Date Seeds and Grass" Master's thesis, King Fahd University of Petroleum & Minerals, 2014; pp. 1-138.

* cited by examiner

FIG. 5

DATE TREE WASTE-BASED COMPOUND FIBROUS LCMS

CROSS-REFERENCE TO RELATED APPLICATIONS

This application is a divisional of and claims priority from U.S. Non-Provisional application Ser. No. 15/436,129 filed Feb. 17, 2017, and titled "DATE TREE WASTE-BASED COMPOUND FIBROUS LCMS," which claims priority from U.S. Provisional Application No. 62/356,862 filed Jun. 30, 2016, and titled "DATE TREE WASTE-BASED COMPOUND FIBROUS LCMS," each of which are incorporated by reference in their entirety for the purposes of United States patent practice.

BACKGROUND

Field of the Disclosure

The present disclosure generally relates to controlling lost circulation in a wellbore during drilling with a drilling fluid. More specifically, embodiments of the disclosure relate to a lost circulation material (LCM).

Description of the Related Art

Lost circulation is one of the frequent challenges encountered during drilling operations. Lost circulation can be encountered during any stage of operations and occurs when drilling fluid (such as drilling mud) pumped into a well returns partially or does not return to the surface. While some fluid loss is expected, excessive fluid loss is not desirable from a safety, an economical, or an environmental point of view. Lost circulation is associated with problems with well control, borehole instability, pipe sticking, unsuccessful production tests, poor hydrocarbon production after well completion, and formation damage due to plugging of pores and pore throats by mud particles. In extreme cases, lost circulation problems may force abandonment of a well.

Lost circulation can occur in various formations, such as naturally fractured formations, cavernous formations, and high permeable formations. Lost circulation can be categorized by the amount of fluid or mud lost as seepage type, moderate type, severe type, and total loss. The extent of the fluid loss and the ability to control the lost circulation with an LCM depends on the type of formation in which the lost circulation occurs. Formations with low permeability zones, that is, those with microscopic cracks and fissures, usually have seepage type lost circulation. Other formations may experience lost circulation if an improper mud weight is used while drilling.

SUMMARY

Lost circulation materials (LCMs) are used to mitigate the lost circulation by blocking the path of the drilling fluid (such as drilling mud) into the formation. The type of LCM used in a lost circulation situation depends on the extent of lost circulation and the type of formation. Different types of LCMs such as granular, fibrous and flaky materials are frequently used either alone or in combination to control loss of circulation. For example, fibrous LCMs may include cedar fibers or synthetic fibers to control loss of circulation.

Costs incurred in loss circulation situations may be due to losses of drilling fluids, losses of production, and the costs of LCMs, including importation of LCMs to drilling locations. Additionally, lost circulation can cause environmental problems if drilling fluids or LCMs interact with the environment surrounding the reservoir. The manufacture, use, and disposal of some conventional LCMs may pose a risk to sensitive environments, such as marine environments because they are not biodegradable and can be toxic to marine life. Additionally, the purchase and importation of LCMs to drilling locations may be expensive and time-consuming.

In some embodiments, a method to control lost circulation in a lost circulation zone in a wellbore is provided. The method includes introducing an altered drilling fluid into the wellbore such that the altered drilling fluid contacts the lost circulation zone and reduces a rate of lost circulation into the lost circulation zone. The altered drilling fluid includes a drilling fluid and a lost circulation material (LCM). The LCM includes a plurality of date tree waste fibers produced from date tree waste. The date tree waste is waste from date palm processing. In some embodiments, the altered drilling fluid consists of the drilling fluid and the LCM. In some embodiments, the LCM consists of the plurality of date tree waste fibers produced from date tree waste. In some embodiments, the date tree waste includes at least one of: date tree trunks, date tree rachis, date tree leaves, date tree leaflets, and date tree roots. In some embodiments, the date tree waste fibers include fibers produced from at least one of: date tree trunks, date tree rachis, date tree leaves, date tree leaflets, and date tree roots. In some embodiments, the plurality of date tree waste fibers are a concentration of at least 30 pounds-per-barrel (ppb) in the altered drilling fluid. In some embodiments, the reduced rate of lost circulation of a fluid portion of the altered drilling fluid is zero. In some embodiments, each of the plurality of date tree fibers has a length in the range of 5 millimeters (mm) to 15 mm. In some embodiments, each of the plurality of date tree fibers has a diameter in the range of 0.5 mm to 0.8 mm. In some embodiments, each of plurality of date tree fibers has an aspect ratio in the range of 6 to 30.

Additionally, in some embodiments, an altered drilling fluid is provided. The altered drilling fluid includes a drilling fluid and a lost circulation material (LCM) having a plurality of date tree waste fibers produced from date tree waste. The date tree waste includes waste from date palm processing. In some embodiments, the date tree waste includes at least one of: date tree trunks, date tree rachis, date tree leaves, date tree leaflets, and date tree roots. In some embodiments, the date tree waste fibers include fibers produced from at least one of: date tree trunks, date tree rachis, date tree leaves, date tree leaflets, and date tree roots. In some embodiments, the plurality of date tree waste fibers are a concentration of at least 30 pounds-per-barrel (ppb) in the altered drilling fluid. In some embodiments, the plurality of date tree waste fibers includes a plurality of untreated date tree waste fibers. In some embodiments, each of the plurality of date tree fibers has a length in the range of 5 millimeters (mm) to 15 mm. In some embodiments, each of the plurality of date tree fibers has a diameter in the range of 0.5 mm to 0.8 mm. In some embodiments, each of plurality of date tree fibers has an aspect ratio in the range of 6 to 30.

In some embodiments, a lost circulation material (LCM) composition is provided. The LCM composition includes a plurality of date tree waste fibers produced from date tree waste. The date tree waste includes waste from date palm processing. In some embodiments, the date tree waste includes at least one of: date tree trunks, date tree rachis, date tree leaves, date tree leaflets, and date tree roots. In some embodiments, the date tree waste fibers include fibers produced from at least one of: date tree trunks, date tree rachis, date tree leaves, date tree leaflets, and date tree roots. In some embodiments, the plurality of date tree waste fibers includes a plurality of untreated date tree waste fibers. In some embodiments, each of the plurality of date tree fibers has a length in the range of 5 millimeters (mm) to 15 mm. In some embodiments, each of the plurality of date tree fibers has a diameter in the range of 0.5 mm to 0.8 mm. In some embodiments, each of plurality of date tree fibers has an aspect ratio in the range of 6 to 30.

In some embodiments, a method of forming a lost circulation material (LCM) is provided. The method includes grinding date tree waste to produce a plurality of date tree waste fibers. The date tree waste is waste from date palm processing and further includes at least one of: date tree trunks, date tree rachis, date tree leaves, date tree leaflets, and date tree roots. The method also includes mixing the plurality of date tree waste fibers to form an homogenous mix of the date tree waste fibers, such that LCM includes the homogenous mix. In some embodiments, the method includes chopping the date tree waste before grinding the date tree waste. In some embodiments, the method includes washing the date tree waste before chopping the date tree waste. In some embodiments, the method includes crushing the date tree waste to produce the plurality of date tree waste fibers, such that the crushing is performed during the grinding. In some embodiments, the method includes sun drying the homogenous mix of date tree waste fibers for a time period at atmospheric conditions.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments set forth in the disclosure. Rather, these embodiments are provided so that this disclosure will be thorough and complete, and will fully convey the scope of the disclosure to those skilled in the art.

As a wellbore is drilled, a drilling fluid is continuously pumped into the wellbore to clear and clean the wellbore and the filings. The drilling fluid is pumped from a mud pit into the wellbore and returns again to the surface. A lost circulation zone is encountered when the flow rate of the drilling fluid that returns to the surface is less than the flow rate of the drilling fluid pumped into the wellbore, and it is this reduction or absence of returning drilling fluid that is referred to as lost circulation.

Embodiments of the disclosure include a date tree waste LCM that includes date tree waste fibers to mitigate or prevent lost circulation in a well, as well as provide seepage control and minimize or prevent fluid loss. As used in the disclosure, the term date tree waste refers to the waste produced from processing date trees (also referred to as "date palms") in the production of date fruits (also referred to as "dates"). The date tree waste fibers may include, by way of example, fibers from one or more of the following: date tree trunks, date tree rachis, date tree leaflets, date tree panicles, and date tree roots. In some embodiments, the date tree waste LCM includes a combination of multiple types of date tree waste fibers having different physio-mechanical properties, such as any combinations of highly flexible trunk fibers, moderately flexible rachis fibers, modest tear and shear resistance date tree leaflet fibers, high tear and shear resistance panicle and date tree root fibers. In some embodiments, the date tree waste LCM includes fibers having lengths in the range of about 5 millimeters (5 mm) to about 15 mm. In some embodiments, the date tree waste LCM includes fibers having lengths in the range of 5 mm or less to about 15 mm or greater. In some embodiments, the date tree waste LCM includes fibers having diameters in the range of about 0.5 mm to about 0.8 mm. In some embodiments, the date tree waste LCM includes fibers having diameters in the range of 0.5 mm or less to about 0.8 mm or greater. In some embodiments, the date tree waste LCM includes fibers with an aspect ratio range of 6 to about 30. In some embodiments, the date tree waste LCM includes fibers with an aspect ratio in range of about 6 or less to about 30 or greater. As used in the disclosure, the term "aspect ratio" refers to a ratio of fiber length to diameter.

Figure 1:
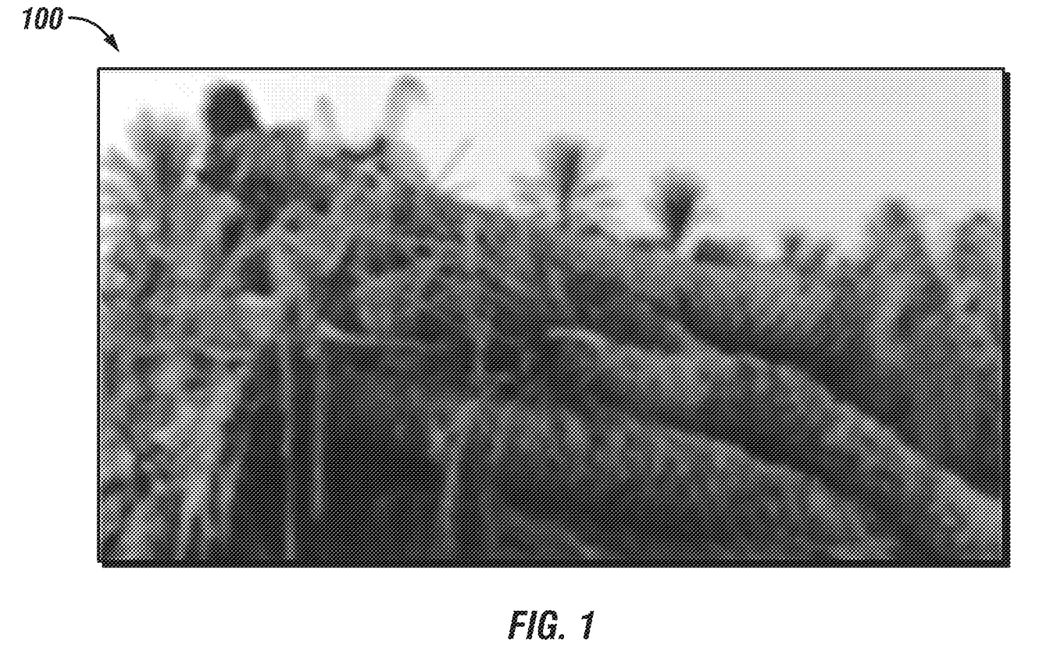
FIG. 1 is a photograph of date tree waste in accordance with an embodiment of the disclosure.
Figure 2:
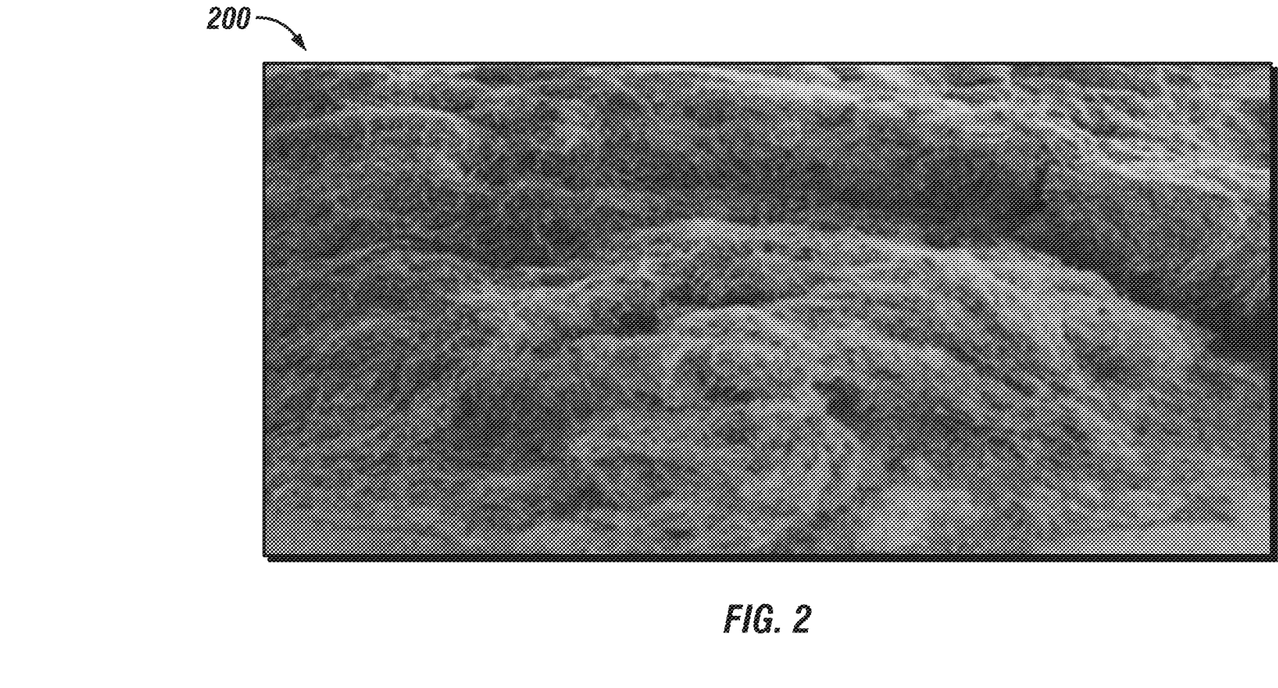
FIG. 2 is a photograph of date tree waste fibers produced from the date tree waste shown in FIG. 1 in accordance with an embodiment of the disclosure.

FIG. 1 is a photograph of deceased date trees 100 showing date tree waste in accordance with an example embodiment of the disclosure. As shown in FIG. 1, such date tree waste may include trunks (for example, the trunk body), leaf stalks, leaflets, roots, etc. In some embodiments, the date tree waste may include panicles (now shown) from the date tree. FIG. 2 is a photograph 200 of fibers produced from the date tree waste shown in FIG. 1 after sun drying.

As described in the disclosure, the presence of fibers of various aspect ratios (for example, an aspect ratio range of 6 to about 30) and various mechanical properties (for example, tear, shear resistance, rupture resistance, ductility, and so on) may enable the date tree waste LCM to provide highly stable flow barriers to mitigate or prevent the loss of whole mud while drilling or the loss of cement slurry while cementing a well. The flexible, semi-rigid, and shear and tear resistant fibers of the date tree waste LCM may exhibit networking, entangling, entrapping, and interweaving activity while under the influence of dynamic flow, external forces, external pressures, or any combination there. This activity may enable the date tree waste LCM to form a relatively low porosity (that is, capable of stopping the loss of whole mud or allowing a negligible amount of mud loss) fibrous mat-type seal at the mouth of fractures and gaps in a loss zone, within narrow spaces of the fractures and gaps of the loss zone, or both. Further, the fibrous mat-like seal may allow for the infiltration and deposition of mud solids at the seal interface due to the partial escape of some fluid of the fluid phase of the mud under overbalance pressure for example. The partial escape of some fluid the fluid phase of the mud may allow for the creation of a mudcake-like barrier similar to the mudcake (also referred to as a "filter cake") deposited on the borehole wall of rock formations. The creation of a mudcake-like barrier on the fibrous mat-like seal may further mitigate or prevent the loss of whole mud while drilling.

As further described in the disclosure, the properties of the date tree waste LCM may eliminate the need to use other types of LCMs for controlling fluid losses in potential loss zones. Moreover, the combination of fibers of various lengths, diameters, and aspect ratios may enable the date tree waste LCM to seal and block fracture sizes from about 500 microns to about 12 mm. The date tree waste LCM may prevent or alleviate lost circulation during drilling or cementing operations without any prior knowledge of the loss zone characteristics such as pore size, fracture size, gap size, fracture density, fracture path tortuosity, and the length. As mentioned supra, the networking, entangling, entrapping, and interweaving activity of the fibers combination may result in the creation of a low porosity fibrous mat-like flow arrester at the mouth or within fractures, gaps, and other loss zone structures. The low porosity fibrous mat-like structure (for example, a seal) may prevent the loss of whole mud during drilling operations or cement slurry during cementing operations. Additionally, the fibrous mat-like structure may provide for a fortified flow barrier with sufficient mechanical strength and load bearing capacity to maintain its integrity at downhole conditions (for example, the date tree waste LCM may be capable of stopping the loss of whole mud or only allow negligible mud losses at a pressure of about 1000 pound per square inch (psi) and a temperature of 212° F. in a simulated pore plugging test).

EXAMPLES

The following examples are included to demonstrate embodiments of the disclosure. It should be appreciated by those of skill in the art that the techniques and compositions disclosed in the example which follows represents techniques and compositions discovered to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

The following non-limiting examples of a date tree waste LCM were prepared and evaluated against commercially available LCMs. Plugging efficiency tests were conducted on the date fruit cap LCM and commercially available LCMs using a 2 mm slotted disc and a Permeability Plugging Tester (also referred to as "PPT" or "Pore Plugging Test" apparatus) manufactured by OFI Testing Equipment, Inc., of Houston, Tex., USA. The tests were conducted at conditions of about 250° F. and about 1000 psi differential pressure. For the plugging efficiency tests, the date fruit cap LCM and commercially available LCMs were incorporated into a 65 pounds per cubic foot (pcf) bentonite mud. The composition of the 65 pcf bentonite mud with mud components expressed in pounds-per-barrels (lb/bbl) is shown in Table 1:

TABLE 1

Composition of 65 pcf bentonite mud

| Mud Component | Lb/bbl |
|---|---|
| Water | 340.67 |
| Bentonite | 25.00 |
| Caustic Soda | 0.25 |
| Soda Ash | 0.25 |

The date tree waste LCM and different commercially available LCMs were tested using the Permeability Plugging Tester apparatus and the following plugging efficiency test procedure:

1. Set the temperature controller/thermostat to the testing temperature;
2. Check the condition of the O-rings in the groove at the top of the test cell of the Permeability Plugging Tester apparatus and in the cell end cap and replace the O-rings if needed;
3. Apply a thin coating of high temperature grease to all the O-rings, including the two O-rings on the piston of the Permeability Plugging Tester apparatus;
4. Screw the T-bar of the Permeability Plugging Tester apparatus into the piston, install into the bottom end of the test cell, position the piston about 1 inch into the cell bore, and remove the T-bar;
5. Add a volume of hydraulic oil to the test cell using the hydraulic hand pump of the Permeability Plugging Tester apparatus;
6. Install all the O-rings and secure the end cap of the cell in position such that oil flows from the hole in the end cap to ensure no air is trapped;
7. Install the valve stem into the bottom end cap of the cell, tighten the valve stem, and disconnect from the hydraulic hand pump of the Permeability Plugging Tester apparatus;
8. Place the cell upright on a suitable stand;
9. Pour a test sample of a homogenous mixture of 275 ml of the 65 pcf bentonite mud and 30 grams of an LCM into the test cell;
10. Install an O-ring into the top of the cell below the 2 mm slotted disc;
11. Place the 2 mm slotted disc on top of the O-ring;
12. Insert the end cap on the top of the disc, screw down the threaded retaining ring, and fully tighten;
13. Tighten the top stem of the test cell;
14. Place the cell into the heating jacket of the Permeability Plugging Tester apparatus;
15. Connect a pressure hose from the hydraulic hand pump to the bottom of the test cell via a quick connector and ensure the bottom stem is closed;
16. Connect the back pressure hose/sample collector to the top stem of the test cell, ensuring that the locking pin is in place, close the pressure relief valve on the side of the hydraulic hand pump, apply the testing pressure via the back pressure regulator to the top of the test cell, and close the top valve.
17. Place a thermometer into the hole at the top of the test cell. wait until the testing temperature is reached, and monitor the cell pressure while heating and bleed off pressure if necessary by opening the pressure relived valve on the side of the hydraulic hand pump;
18. Once the test sample has reached the testing temperature, pump the hydraulic hand pump until the pump gauge shows the testing pressure plus the required back pressure;
19. Apply the required back pressure to the top of the cell, open the top valve, and pump the hydraulic hand pump to reestablish the testing pressure;
20. To determine the spurt volume, collect the fluid from the back pressure collector in a measuring cylinder and record the amount, ensuring that all the fluid has been expelled;
21. Collect the fluid periodically over a 30 minute time period and check the back pressure gauge to ensure that the pressure remains less than the pressure threshold (about 3000 psi) of the built-in safety disc of the Permeability Plugging Tester apparatus and avoid expulsion of hot hydraulic oil;
22. Record the spurt loss, total leak off, and PPT values over the 30 minute time period and record the cake thickness after dismantling the test cell.

The date tree waste LCM was tested against a commercially available cellulosic fiber and flake LCM, STOP-LOSS® manufactured by Drilchem of Jakarta, Indonesia. Table 5 shows the results of plugging efficiency tests for STOPLOSS® at a 30 pounds-per-barrel (ppb) concentration in the 65 pcf bentonite mud and the results of plugging efficiency tests for the date tree waste LCM at a 30 ppb concentrations in the 65 pcf bentonite mud, with the spurt loss, fluid loss, total leak off, and PPT value measured in cubic centimeters (cc) and the cake thickness measured in mm:

TABLE 2

Plugging Efficiency Test Results for Date Tree Waste
LCM and Commercially Available LCM

| Mud | LCM | Concentration | Spurt loss (cc) | Fluid loss (cc) | Total Leak off (cc) | Cake Thickness (mm) | PPT Value (cc) |
|---|---|---|---|---|---|---|---|
| 65 pcf bentonite mud | Date tree waste LCM | 30 ppb | 1 | 0 | 1 | 11.9 | 2 |
| 65 pcf bentonite mud | STOPLOSS ® | 30 ppb | 0.7 | 16 | 16.7 | 3.97 | 33.4 |

As shown in Table 2, the 30 ppb concentration of the date tree waste LCM controlled the loss of the whole bentonite mud with negligible mud losses. Table 2 shows superior performance by the date tree waste LCM as compared to the STOPLOSS® commercially available LCM. As shown by the negligible spurt loss, zero fluid loss, and negligible leak off, the 30 ppb concentration of the date tree waste LCM demonstrated the ability to seal a potential loss zone quickly with a negligible loss of whole mud into the loss zone under a 1000 psi differential pressure.

The date tree waste LCM was also tested against a commercially available proprietary fiber and flake LCM, SOLU-SEAL™ manufactured by Drilchem of Jakarta, Indonesia. Table 5 shows the results of plugging efficiency tests for SOLU-SEAL™ at a 30 ppb concentration in the 65 pcf bentonite mud and the results of plugging efficiency tests for the date tree waste LCM at a 30 ppb concentrations in the 65 pcf bentonite mud, with the spurt loss, fluid loss, total leak off, and PPT value measured in cc and the cake thickness measured in mm:

TABLE 3

Plugging Efficiency Test Results for Date Tree Waste
LCM and Commercially Available LCM

| Mud | LCM | Concentration | Spurt loss (cc) | Fluid loss (cc) | Total Leak off (cc) | Cake Thickness (mm) | PPT Value (cc) |
|---|---|---|---|---|---|---|---|
| 65 pcf bentonite mud | Date tree waste LCM | 30 ppb | 1 | 0 | 1 | 11.9 | 2 |
| 65 pcf bentonite mud | SOLU-SEAL ™ | 30 ppb | 0 | 2 | 2 | 6.35 | 4 |

Here again, as shown in Table 3, the 30 ppb concentration of the date tree waste LCM controlled the loss of the whole bentonite mud with negligible mud losses. Table 3 shows similar performance by the date tree waste LCM as compared to the SOLU-SEAL™ commercially available LCM. As shown by the negligible spurt loss, zero fluid loss, and negligible leak off, the 30 ppb concentration of the date tree waste LCM demonstrated suitability as an alternative to the commercially available SOLU-SEAL™ LCM for application in controlling mud losses in a loss zone of a well.

Figure 3:
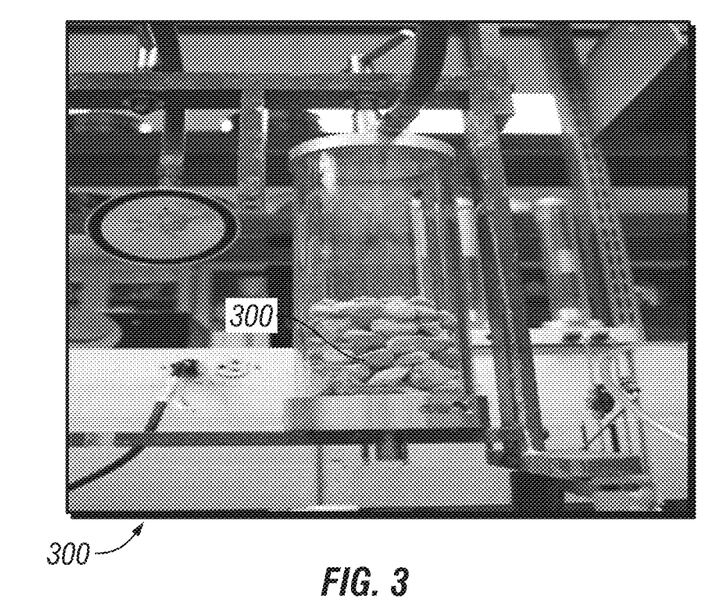
FIG. 3 is a photograph of a highly permeable test bed testing apparatus in accordance with an embodiment of the disclosure.

In addition the plugging efficiency test described supra, further tests were performed to compare the performance of the date tree waste LCM with the commercially available STOPLOSS® LCM and the commercially available SOLU-SEAL™ LCM. The first additional test was conducted by simulating an extremely high permeable test bed representing a super-K loss zone by using a pebble bed having pebble sizes in the range of about 20 mm to about 25 mm. The super-K loss zone simulation test evaluates the ability of an LCM to control losses in extremely high permeable formations. As used in the disclosure, the term "super-K" refers to a zone of extremely high permeability of greater than 500 millidarcy (md). FIG. 3 is a photograph 300 of the extremely high permeable test bed testing apparatus and the pebble bed 302. The components of the testing apparatus are described in more detail infra with reference to FIGS. 4A-4E.

The super-K loss zone simulation test was performed on the date tree waste LCM, the STOPLOSS® commercially available LCM, and the SOLU-SEAL™ commercially available LCM to determine whether each tested LCM was able to prevent mud loss in the pebble bed. The test was performed using the 65 pcf bentonite mud as the carrier fluid and an application of about 100 psi differential pressure at ambient temperature for a time period of about 30 minutes.

Table 4 shows the results of the super-K loss zone simulation test for the date tree waste LCM at a 30 ppb concentration in the 65 pcf bentonite mud, for the STOPLOSS® commercially available LCM at a 30 ppb concentration in the 65 pcf bentonite mud, and the SOLU-SEAL™ commercially available LCM at a 30 ppb concentration in the 65 pcf bentonite mud:

TABLE 4

Super-K Loss Zone Simulation Test Results for Date Tree Waste LCM and Commercially Available LCMs

| Mud | Test Temperature and Pressure | Test Bed | LCM | Concentration | Test Results |
|---|---|---|---|---|---|
| 65 pcf bentonite mud | Ambient Temperature and 100 psi | 20-25 mm Pebble Bed | Date tree waste LCM | 30 ppb | Able to Prevent Mud Loss |
| 65 pcf bentonite mud | Ambient Temperature and 100 psi | 20-25 mm Pebble Bed | STOPLOSS® | 30 ppb | Able to Prevent Mud Loss |
| 65 pcf bentonite mud | Ambient Temperature and 100 psi | 20-25 mm Pebble Bed | SOLU-SEAL™ | 30 ppb | Able to Prevent Mud Loss |

As shown in Table 4, the date tree waste LCM was able to prevent mud loss in the pebble bed at 100 psi differential pressure over a time period of about 30 minutes, thus illustrating the ability of the date tree waste LCM to control losses in an extremely high permeable formation. As shown in Table 4, the date tree waste LCM also has similar performance in an extremely high permeable formation to the STOPLOSS® commercially available LCM, and the SOLU-SEAL™ commercially available LCM.

Figure 4A:
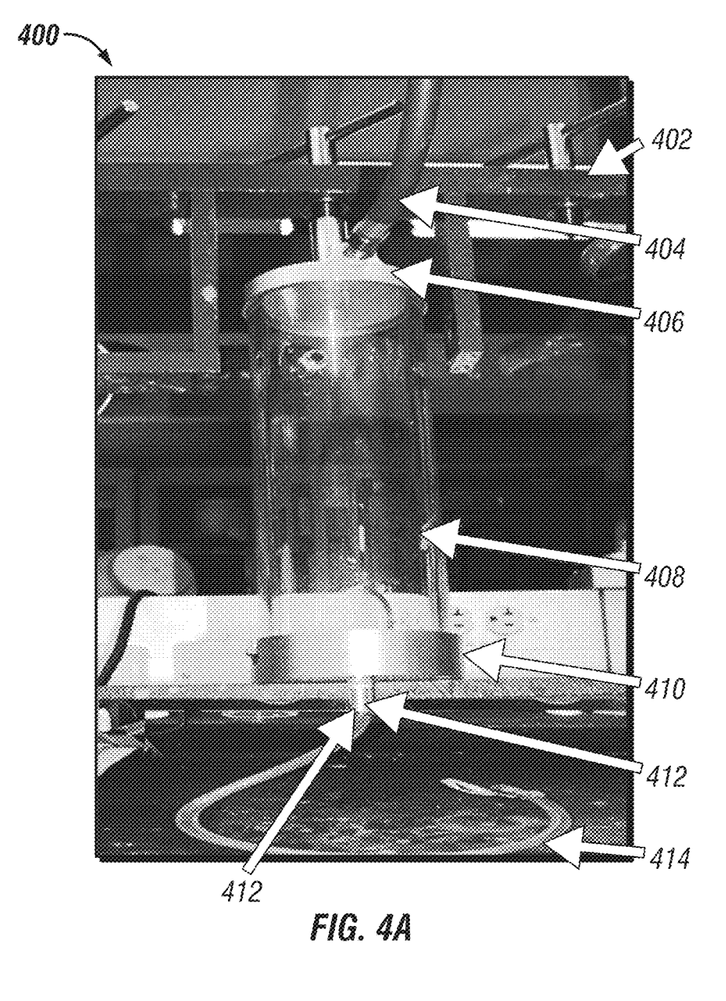
FIGS. 4A-4E are photographs of a testing apparatus and associated components in accordance with an embodiment of the disclosure.

The second additional test was conducted by simulating a loss zone with large fractures using a test cell with a 10 mm exit hole. FIGS. 4A-4E are photographs of a testing apparatus 400 and associated components having a test cell with a 10 mm exit hole and a flexible tube having a length of at least 3 feet (ft) to simulate a loss zone having large fractures. As shown in FIG. 4A, the testing apparatus 400 includes a mounting stand 402, an air pressure inlet line 404, a top lid 406, an LCM test cell 408, a bottom lid 410, a 10 mm orifice 412 in the bottom lid, and a 10 mm diameter flexible tube 414 having a length of at least 3 ft. The top lid 406 and the bottom lid 410 may close and seal the LCM test cell 408. The bottom lid 410 may include a connector 416 to connect the flexible tube 414.

Figure 4B:
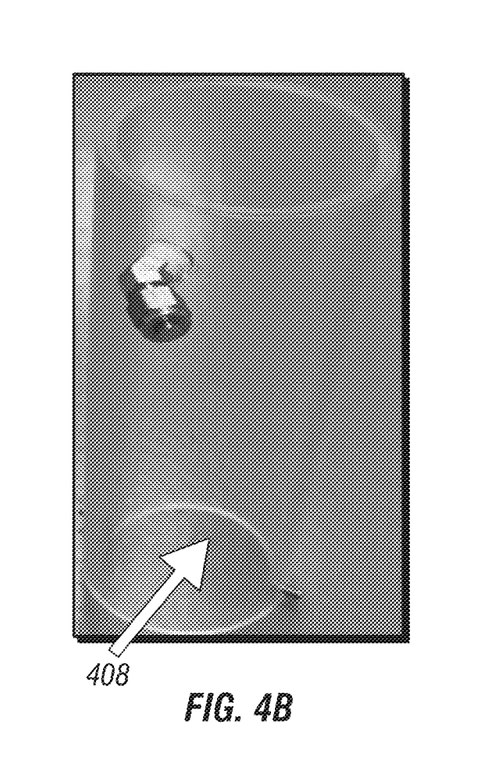
Figure 4C:
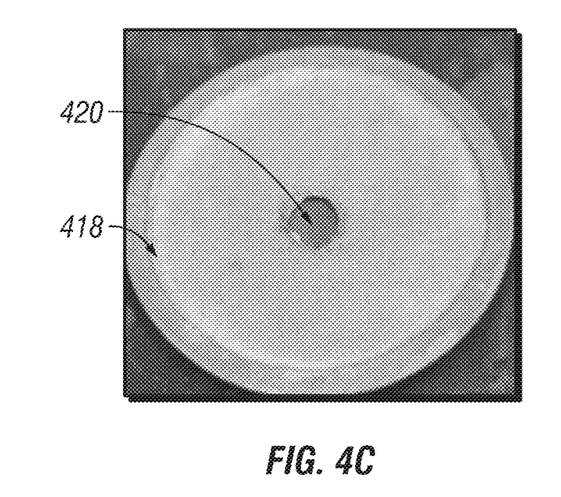
Figure 4D:
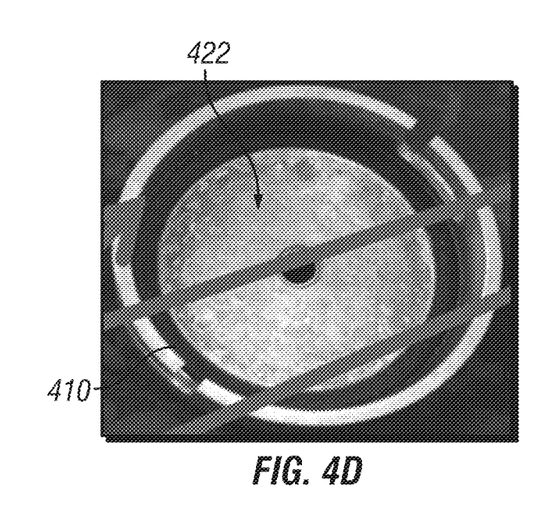
Figure 4E:
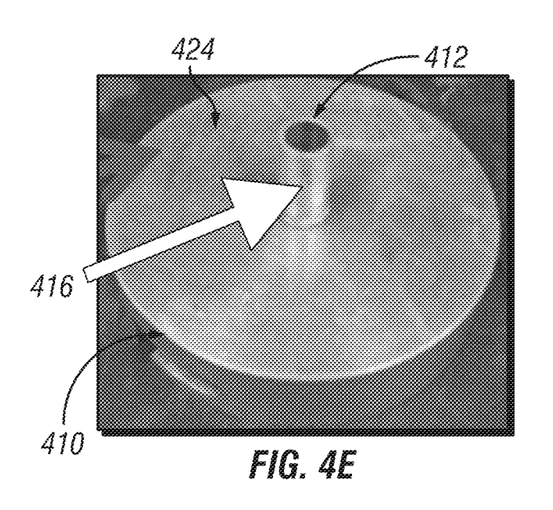

FIGS. 4B-4E depict individual components of the testing apparatus 400. FIG. 4B is a photograph of a perspective view of the LCM test cell 408. FIG. 4C is a photograph of a wire screen 418 having a 10 mm orifice 420. The wire screen 418 is disposed on the inner surface of the bottom lid 410 before attaching the bottom lid 410 to the LCM test cell 408. FIG. 4D is a photograph of a top view of the bottom lid 410 illustrating the inner surface 422 of the bottom lid 410. FIG. 4E is a bottom view of the bottom lid 410 illustrating an outer surface 424 of the bottom lid 410, the connector 416, and the 10 mm orifice 412.

The loss zone with large fractures simulation test was performed on the date tree waste LCM, the STOPLOSS® commercially available LCM, and the SOLU-SEAL™ commercially available LCM to determine whether each tested LCM was able to prevent mud loss through the 10 mm exit orifice 412. The test was performed using the 65 pcf bentonite mud as the carrier fluid and with an application of about 100 psi differential pressure at ambient temperature for a time period of about 30 minutes.

Table 5 shows the results of the loss zone with large fractures simulation test for the date tree waste LCM at a 30 ppb concentration in the 65 pcf bentonite mud, for the STOPLOSS® commercially available LCM at a 30 ppb concentration in the 65 pcf bentonite mud, and the SOLU-SEAL™ commercially available LCM at a 30 ppb concentration in the 65 pcf bentonite mud:

TABLE 5

Loss Zone with Large Fractures Simulation Test Results for Date Tree Waste LCM and Commercially Available LCMs

| Mud | Test Temperature and Pressure | Test Bed | LCM | Concentration | Test Results |
|---|---|---|---|---|---|
| 65 pcf bentonite mud | Ambient and 100 psi | Test cell with 10 mm exit orifice | Date tree waste LCM | 30 ppb | Able to Prevent Mud Loss |
| 65 pcf bentonite mud | Ambient and 100 psi | Test cell with 10 mm exit orifice | STOPLOSS® | 30 ppb | Failed to Prevent Mud Loss |
| 65 pcf bentonite mud | Ambient and 100 psi | Test cell with 10 mm exit orifice | SOLU-SEAL™ | 30 ppb | Failed to Prevent Mud Loss |

As shown in Table 5, the date tree waste LCM was able to prevent mud loss through the 10 mm exit orifice at 100 psi differential pressure over a time period of about 30 minutes, thus illustrating the ability of the date tree waste LCM to control losses in loss zones with large fractures. During the test, the application of 100 psi pressure over 30 minute time period was unable to push any of the 65 pcf bentonite mud through the exit orifice. In contrast, the 30 ppb concentrations of the commercially available LCMs were unable to control the loss of whole mud through the 10 mm exit orifice. During the test of the commercially available LCMs, the application of 100 psi pressure resulted in an immediate loss of the 65 pcf bentonite mud through the exit orifice. Thus, as summarized in Table 5, the date tree waste LCM has superior performance in loss zones with large fractures as compared to the STOPLOSS® commercially available LCM, and the SOLU-SEAL™ commercially available LCM.

Date Tree Waste LCM Manufacture and Use

In some embodiments, a date tree waste LCM may include date tree waste fibers obtained from date tree waste. In some embodiments, the date tree waste fibers may include fibers from any combination of the following date tree waste: date tree trunks, date tree rachis, date tree leaves, date tree leaflets, and date tree roots. In other embodiments, alternative or additional date tree waste may be used to produce the date tree waste fibers. The date tree waste may be produced as a waste by-product from date processing. The date tree waste may be obtained from date processing plants to provide sustainable source of material for the date tree waste LCM. Moreover, local sources of date tree waste may reduce the cost of imported LCM products, components, or both. In some embodiments, the date tree waste may be obtained from the species *phoenix dactylifera*. It should be appreciated that, in some embodiments, the date tree waste may be obtained from genetically modified date trees (that is, genetically modified organisms (GMOs)). In some embodiments, the date tree waste is prepared by cleaning the date tree waste before use as an LCM, such as by washing the date tree waste.

In some embodiments, the date tree waste LCM includes date tree waste fibers having lengths in the range of 5 millimeters (5 mm) to about 15 mm. In some embodiments, the date tree waste LCM includes fibers having lengths less than 5 mm and greater than 15 mm. For example, a date tree waste LCM may include any combination of date tree waste fibers having lengths of 4 mm or greater, 5 mm or greater, 6 mm or greater, 7 mm or greater, 8 mm or greater, 9 mm or greater, 10 mm or greater, 11 mm or greater, 12 mm or greater, 13 mm or greater, 14 m or greater, 15 mm or greater, and 16 mm or greater. In some embodiments, the date tree waste LCM includes fibers having diameters in the range of 0.5 mm to about 0.8 mm. In some embodiments, the date tree waste LCM includes fibers having diameters in the range of 0.5 mm or less to about 0.8 mm or greater. For example, a date tree waste LCM may include any combination of date tree waste fibers having diameters of 0.4 mm or greater, 0.5 mm or greater, 0.6 mm or greater, 0.7 mm or greater, 0.8 mm or greater, and 0.9 mm or greater. In some embodiments, the date tree waste LCM includes fibers with an aspect ratio range of about 6 to about 30. In some embodiments, the date tree waste LCM includes fibers with an aspect ratio range of 6 or less to about 30 or greater. For example, the date tree waste LCM includes any fibers with an aspect ratio of 5 or greater, 6 or greater, 10 or greater, 15 or greater, 20 or greater, 25 or greater, 30 or greater, and 31 or greater.

In some embodiments, the date tree waste may include untreated date tree waste, thus preserving the environmentally-friendly and biodegradable properties of the manufacturing process, the fibers, and the resulting LCM composition. As used in the disclosure, the term "untreated" or "without treating" refers to not treated with alkali or acid, not bleached, not chemically altered, not oxidized, and without any extraction or reaction process other than possibly drying of water. The term "untreated" or "without treatments" does not encompass grinding or heating to remove moisture but does encompass chemical or other processes that may change the characteristics or properties of the fibers. In such embodiments, the date tree waste may be manufactured without treating before, during, or after crushing, grinding, drying, or any other processing.

In some embodiments, the date tree waste LCM may be added directly to a drilling fluid, such as a drilling mud, to create an altered drilling fluid having the date tree waste LCM. For example, in some embodiments, the date tree waste LCM may be added to (for example, blended with) an oil-based drilling mud or a water-based drilling mud. In some embodiments, the date tree waste LCM may be added at the mud pit of a mud system. After addition of the date tree waste LCM to a drilling fluid, the altered drilling fluid may be circulated at a pump rate effective to position the altered drilling fluid into contact with a lost circulation zone in a wellbore, such that the date tree waste LCM alters the lost circulation zone (for example, by entering and blocking porous and permeable paths, cracks, and fractures in a formation in the lost circulation zone, such as forming a structure in a mouth or within a fracture).

As noted in the disclosure, the mechanical properties of the date tree waste LCM may prevent degradation of the date tree waste LCM while circulating downhole as a fluid loss additive or formation strengthening material. Moreover, the eco-friendly, non-toxic, and environmentally friendly properties of the date tree waste LCM may minimize or prevent any environmental impact, any effect on ecosystems, habitats, population, crops, and plants surrounding the drilling site where the date tree waste LCM is used.

Figure 5:
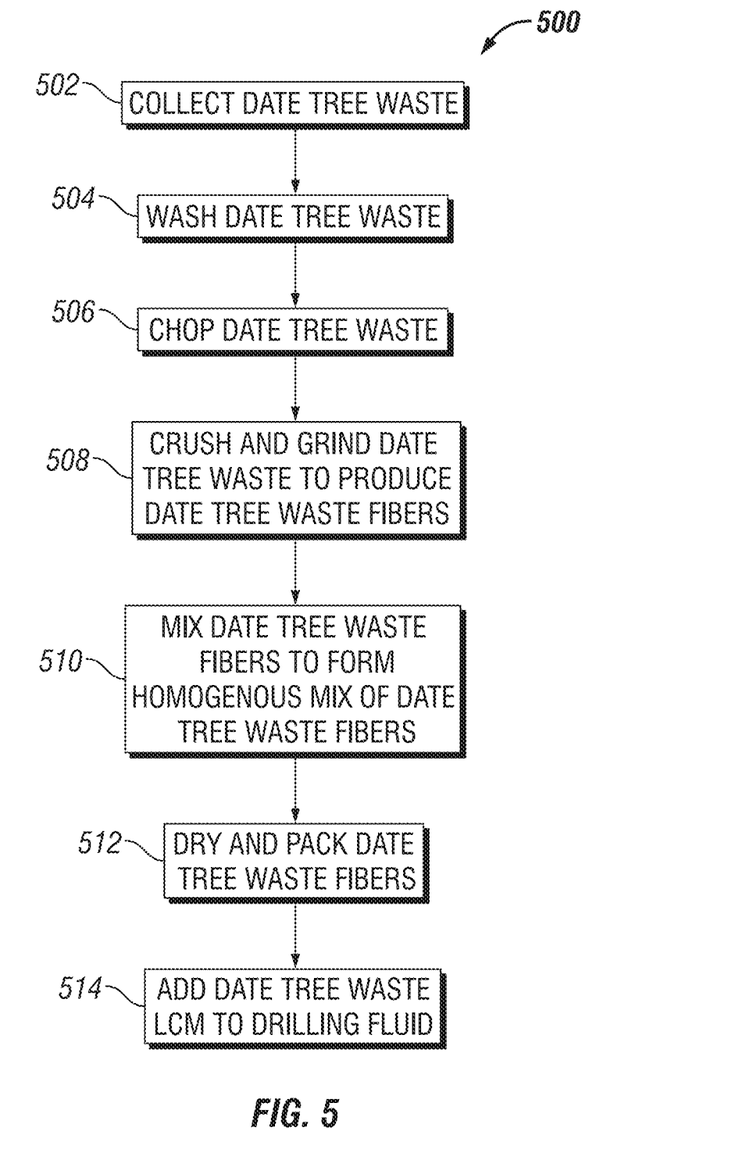
FIG. 5 is a flowchart of a process for manufacturing and using a date tree waste LCM in accordance with an embodiment of the disclosure.

FIG. 5 depicts a process 500 for the production and use of a date tree waste LCM in accordance with an example embodiment of the disclosure. As shown in FIG. 5, date tree waste may collected (block 502), such as from a date processing facility. In some embodiments, date tree waste may be collected from a date processing facility and transported to another facility for processing as described in the disclosure. In some embodiments, the collected date tree waste may include any combination of the following: date tree trunks, date tree rachis, date tree leaves, date tree leaflets, and date tree roots. Next, the date tree waste may be washed to remove dirt, dust, and other foreign substances (block 504). In some embodiments the date tree waste may be washed using a high pressure water jet to remove dirt, dust, and other foreign substances.

Next, the date tree waste may be chopped into smaller pieces (block 506). For example, the date tree waste may be chopped for subsequent ease of handling. In some embodiments, the date tree waste may be chopped manually using a suitable chopping tool. In other embodiments, the date tree waste may be chopped automatically via a suitable machine. The chopped date tree waste may then be crushed and grinded to produce date tree waste fibers (block 508). In some embodiments, the chopped date tree waste may be crushed and ground using a suitable commercial crusher and grinder that produce a specific range of fiber sizes (for example, length and diameter).

The date tree waste fibers may then be mixed to form a homogenous mix of fibers (block 510). In some embodiments, the homogenous mix of date tree waste fibers may be dried and packed for transportation and use (block 512). For example, the date tree waste fibers may be packed in paper bags containing about 25 kilograms (kg) of date tree waste fibers. In some embodiments, the date tree waste fibers may be dried using a sun drying process over a time period in atmospheric conditions. In some embodiments, a suitable amount of packed date tree waste fibers may then be transported to an oil and gas operations site for use as a date tree waste LCM.

In some embodiments, the date tree waste LCM may be added directly to a drilling fluid (block 514), such as a drilling mud, to create an altered drilling fluid having the date tree waste LCM. For example, in some embodiments, the date tree waste LCM may be added to (for example, blended with) an oil-based drilling mud or a water-based drilling mud. In some embodiments, the date tree waste LCM may be added at the mud pit of a mud system. After addition of the date tree waste LCM to a drilling fluid, the altered drilling fluid may be circulated at a pump rate effective to position the drilling fluid into contact with a lost circulation zone in a wellbore, such that the date tree waste LCM alters the lost circulation zone (for example, by entering and blocking porous and permeable paths, cracks, and fractures in a formation in the lost circulation zone). As previously stated, the date tree waste LCM may form a fibrous mat-like structure at openings of paths, cracks, and fractures in a loss zone and within narrow spaces of the paths, cracks, and fractures. In some embodiments, the reduced rate of lost circulation may be negligible. In some embodiments, the date tree waste LCM may be introduced via an open ended drill pipe to place the LCM in the lost circulation zone.

In other embodiments, the date tree waste LCM and one or more additional LCMs may be added to a drilling fluid, such as a drilling mud, to create an altered drilling fluid having the LCMs. For example, in some embodiments, the date tree waste LCM and one or more additional LCMs may be added to an oil-based drilling mud or a water-based drilling mud. In other embodiments, the date tree waste LCM may be added to a cement slurry for use in a cementing operation.

The biodegradation properties of the date tree waste fibers of the date tree waste LCM may enable the date fruit cap LCM to easily degrade and disappear from the environment over time and minimize or prevent any environmental impact. Further, the non-toxic properties of the date tree waste fibers may minimize or prevent any effect on ecosystems, habitats, population, crops, and plants surrounding the drilling site where the date tree waste LCM is used.

In some embodiments, the date tree waste LCM may be mixed with a carrier fluid, a viscosifier, or both. In some embodiments, a date tree waste LCM homogenous suspension or pill may be formed. For example, a specific carrier fluid, viscosifier, or combination therefor may be selected to form a homogenous suspension or pill having the date tree waste LCM. In some embodiments, the carrier fluid may be water or an oil-based fluid. In some embodiments, the carrier fluid may be fresh water, sea water, salt water, diesel oil, mineral oil, or synthetic oil. In some embodiments, the viscosifier may be a clay or a polymer. Next, the homogenous suspension may be added to a drilling fluid and used in the manner similar to the date tree waste LCM described in the disclosure.

Ranges may be expressed in the disclosure as from about one particular value, to about another particular value, or both. When such a range is expressed, it is to be understood that another embodiment is from the one particular value, to the other particular value, or both, along with all combinations within said range Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. An altered drilling fluid, consisting of:
   a drilling fluid, wherein the drilling fluid comprises a bentonite mud comprising water, bentonite, caustic soda, and soda ash; and
   a lost circulation material (LCM), wherein the LCM consists of a plurality of date tree waste fibers produced from date tree waste, wherein the date tree waste comprises waste from date palm processing, wherein the date tree waste fibers comprise fibers produced from at least one of: date tree trunks, date tree rachis, date tree leaves, date tree leaflets, and date tree roots, wherein each of the plurality of date tree fibers has a length in the range of 5 millimeters (mm) to 15 mm, a diameter in the range of 0.5 millimeters (mm) to 0.8 mm, and an aspect ratio in the range of 6 to 30, wherein the LCM reduces a rate of lost circulation in a lost circulation zone comprising a fracture size in the range of 10 millimeters (mm) to 12 mm
   wherein the plurality of date tree waste fibers have a concentration of at least 30 pounds-per-barrel (ppb) in the altered drilling fluid.

2. The altered drilling fluid of claim 1, wherein the plurality of date tree waste fibers comprise a plurality of untreated date tree waste fibers.

* * * * *